United States Patent
Heuermann et al.

(10) Patent No.: US 10,711,296 B2
(45) Date of Patent: Jul. 14, 2020

(54) DIRECTIONAL AMPLIFICATION OF RNA

(71) Applicant: SIGMA-ALDRICH CO. LLC, St Louis, MO (US)

(72) Inventors: Kenneth B Heuermann, St Louis, MO (US); Carol A Kreader, St Louis, MO (US); Jaime K Robert, St Louis, MO (US); Brian W Ward, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 352 days.

(21) Appl. No.: 15/550,559

(22) PCT Filed: Mar. 24, 2016

(86) PCT No.: PCT/US2016/024050
§ 371 (c)(1),
(2) Date: Aug. 11, 2017

(87) PCT Pub. No.: WO2016/154455
PCT Pub. Date: Sep. 29, 2016

(65) Prior Publication Data
US 2018/0044723 A1  Feb. 15, 2018

Related U.S. Application Data

(60) Provisional application No. 62/137,677, filed on Mar. 24, 2015.

(51) Int. Cl.
*C12Q 1/6806* (2018.01)
*C12Q 1/6853* (2018.01)
(Continued)

(52) U.S. Cl.
CPC ....... *C12Q 1/6806* (2013.01); *C12N 15/1065* (2013.01); *C12N 15/1096* (2013.01);
(Continued)

(58) Field of Classification Search
CPC ............ C12N 15/1065; C12N 15/1096; C12Q 1/6806; C12Q 1/6853; C12Q 2521/107;
(Continued)

(56) References Cited

U.S. PATENT DOCUMENTS

| 7,229,765 B2 | 6/2007 | Ziman et al. |
| 2010/0029511 A1* | 2/2010 | Raymond .............. C12Q 1/686 506/26 |

(Continued)

OTHER PUBLICATIONS

Enzymatics Exonuclease I product information sheet (Year: 2011).*
(Continued)

*Primary Examiner* — Jeremy C Flinders
(74) *Attorney, Agent, or Firm* — Benjamin J. Sodey; Sigma-Aldrich Co. LLC

(57) ABSTRACT

Processes, oligonucleotides, and kits for amplifying RNA. In particular, the processes generate and amplify cDNA libraries in which the orientation of the input RNA molecule is preserved in the products. Among the various aspects of the present disclosure is the provision of process for directionally amplifying RNA. The process comprises reverse transcribing at least one RNA molecule in the presence of a plurality of first synthesis primers to generate a plurality of first strands of complementary DNA (cDNA), wherein each of the first synthesis primers comprises a 3' sequence having complementarity to a portion of the RNA molecule, a non-complementary 5' sequence corresponding to one or more amplification primers, and optionally an internal tag sequence comprising a first tag sequence.

12 Claims, 6 Drawing Sheets

(51) Int. Cl.
*C12N 15/10* (2006.01)
*C12N 15/12* (2006.01)

(52) U.S. Cl.
CPC .... *C12Q 1/6853* (2013.01); *C12Y 207/07007* (2013.01); *C12Q 2521/107* (2013.01); *C12Q 2521/331* (2013.01); *C12Q 2525/101* (2013.01); *C12Q 2525/131* (2013.01)

(58) Field of Classification Search
CPC ........ C12Q 2521/331; C12Q 2525/131; C12Y 207/0707
See application file for complete search history.

(56) References Cited

U.S. PATENT DOCUMENTS

| | | |
|---|---|---|
| 2010/0297643 A1 | 11/2010 | Sooknanan |
| 2011/0039732 A1 | 2/2011 | Raymond et al. |
| 2014/0303000 A1 | 10/2014 | Armour |
| 2015/0065378 A1 | 3/2015 | Mathers |

OTHER PUBLICATIONS

Bell (Biotechniques, 2008, 44:834) (Year: 2008).*
International Search Report for PCT/US2016/024050 dated Jun. 24, 2016 (4 pages).

* cited by examiner

Double-Stranded cDNA Product

DIRECTIONAL AMPLIFICATION OF RNA

FIELD OF THE DISCLOSURE

This disclosure relates to amplification of RNA, and in particular to the directional amplification of RNA.

BACKGROUND

A variety of techniques have been developed for preparing directional RNA libraries for sequencing. For example, some methods designed to amplify low quantities of RNA involve the use of "template switching." A single-stranded cDNA library is synthesized from RNA template by hybridization and extension of a primer comprised of a 3'-terminal degenerate sequence or poly-dT sequence, which hybridizes to the RNA template, and a non-hybridized 5' fixed sequence. Upon full-length reverse transcription of the RNA template, cDNA are further extended by the intrinsic 3' terminal transferase activity of reverse transcriptase, typically incorporating a short poly-dC sequence. A second oligonucleotide sequence comprised of the identical 5' fixed sequence as in the cDNA primer and a 3' sequence (typically poly G), terminally blocked to prevent extension, then is hybridized to the terminal transferase-extended poly-dC sequence. This second oligo serves a template for continued extension of the cDNA strand, allowing for affixing of additional sequence that is complementary to the 5' fixed sequence. Following a purification step, a single amplification primer comprised of the 5' fixed sequence is introduced to the cDNA library. The cDNA library is amplified by PCR. This method requires about 100 pg to about 100 ng of rRNA-depleted RNA.

Other RNA amplification methods employ ligation, which reduces amplification efficiency by at least 10-fold. These methods typically require two or more solid phase reversible immobilized (SPRI) paramagnetic bead purification steps. As an example, one method comprises performing first-strand cDNA synthesis with a primer mixture of random degenerate sequence and poly-dT, followed by second-strand synthesis in the presence of dUTP. The resulting double-stranded cDNA library is fragmented and concentrated by SPRI paramagnetic bead purification. Following end repair and A-tailing, sequencing adaptors are ligated to the double-stranded cDNA, and these constructs are digested with uracil DNA glycosylase, eliminating the second cDNA strand. The first strand, with affixed adapter sequences, is purified a second time on SPRI beads, and PCR-amplified. This method requires from about 10 ng to about 100 ng of total RNA.

There is a need, therefore, for amplification methods that are amenable to low RNA input quantities and/or low quality RNA, devoid of purification steps, and clearly indicate amplification product strandedness.

SUMMARY

Among the various aspects of the present disclosure is the provision of process for directionally amplifying RNA. The process comprises reverse transcribing at least one RNA molecule in the presence of a plurality of first synthesis primers to generate a plurality of first strands of complementary DNA (cDNA), wherein each of the first synthesis primers comprises a 3' sequence having complementarity to a portion of the RNA molecule, a non-complementary 5' sequence corresponding to one or more amplification primers, and optionally an internal tag sequence comprising a first tag sequence. The process further comprises replicating the plurality of first strands of cDNA in the presence of a plurality of second synthesis primers to generate a plurality of double-stranded cDNA products, wherein each of the second synthesis primers comprises a 3' sequence having complementarity to a portion of the first strands of cDNA, a 5' sequence corresponding to the one or more amplification primers, and optionally an internal tag sequence comprising a second tag sequence, provided that either one or both of the pluralities of first and second synthesis primers comprises the internal tag sequence such that each double-stranded cDNA product is flanked by either the first or second tag sequence or both the first and second tag sequences. The 3' sequence of the first and the second synthesis primers is random and/or semi-random, and the 5' sequence of the first and the second synthesis primers comprises a majority of non-complementary nucleotides. The last step of the process comprises amplifying the plurality of double-stranded cDNA products in the presence of the one or more amplification primers to generate an amplified library of cDNA products. The process is devoid of purification steps between any of the steps.

In some embodiments, the reverse transcribing step is performed in the presence of Actinomycin D. In further embodiments, the reverse transcribing step, and optionally the second strand synthesis step, is followed by contact with a 3'-5' deoxyribonuclease to degrade unhybridized synthesis primers. In still other embodiments, the 5' sequence of the first and second synthesis primers further comprises at least one binding element for a DNA digesting enzyme. For example, in cases in which the DNA digesting enzyme is a methylation-dependent restriction enzyme, the binding element is hem i-methylated and the one or more amplification primers are methylated, and the process further comprises contacting the amplified library of cDNA products the methylation-dependent restriction enzyme. In some embodiments, the process further comprises incorporating adaptor sequences to the 5' ends of the amplified library of cDNA products.

Another aspect of the present disclosure encompasses an artificial oligonucleotide comprising a 5' sequence corresponding to an amplification primer, an internal tag sequence, and a 3' sequence comprising a random or semi-random sequence.

A further aspect of the present disclosure provides a plurality of artificial oligonucleotides comprising a plurality of first oligonucleotides in which each comprises a 5' sequence corresponding to one or more amplification primers; optionally an internal tag sequence comprising a first tag sequence, and a 3' sequence comprising a random or semi-random sequence, and a plurality of second oligonucleotides in which each comprises a 5' sequence corresponding to the one or more amplification primers; optionally an internal tag sequence comprising a second tag sequence, and a 3' sequence comprising a random or semi-random sequence, provided that either one or both of the pluralities of first and second oligonucleotides comprises the internal tag sequence.

Still another aspect of the present disclosure encompasses a kit for directionally amplifying RNA. The kit comprises a plurality of first synthesis primers in which each first synthesis primer comprises a 5' sequence corresponding to one or more amplification primers, optionally an internal tag sequence comprising a first tag sequence, and a random or semi-random 3' sequence, a plurality of second synthesis primers in which each second synthesis primer comprises a 5' sequence corresponding to the one or more amplification primers, optionally an internal sequence comprising a second tag sequence, and a random or semi-random 3' sequence, provided that either one or both of the pluralities of first and second synthesis primers comprises the internal tag sequence, and the one or more amplification primers.

Other aspects and iterations of the present disclosure are detailed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts annealing between an RNA transcript and the plurality of first synthesis primers. Each synthesis primer comprises a semi-random (semi-degenerate) sequence the 3' end, a first internal barcode sequence, and a constant sequence at the 5' end, wherein the constant sequence corresponds to an amplification primer. FIG. 1B depicts reverse transcription of the RNA into cDNA. FIG. 1C diagrams the double-stranded molecules that remain after digestion with a 3'-5' exonuclease. The arrows to background products that are flanked with the constant primer sequences.

FIG. 2A depicts annealing between the first strand of cDNA and the plurality of second synthesis primers. Each synthesis primer comprises a semi-random (semi-degenerate) sequence the 3' end, a second internal barcode sequence that differs from those in the first oligonucleotides, and a constant sequence at the 5' end that corresponds to an amplification primer. FIG. 2B depicts synthesis of the second strand of cDNA by a non-strand-displacing RNA polymerase. FIG. 2C illustrates the double-stranded cDNA products. The arrow (lower left) points to a background product that is flanked by the constant primer sequences.

FIG. 3A shows heat denaturation of the double-stranded cDNA products in the presence of amplification primers, which are methylated. FIG. 3B illustrates annealing and extension to generate amplicons. Intra-molecular hybridization of complementary 5' and 3' ends forms stem-loop structures, thereby blocking annealing of amplification primers to first strand and second strand synthesis background products. Consequently, the original template and background products are not amplified. FIG. 3C shows an amplified double-stranded cDNA product.

FIG. 4A presents an amplification plot in which curves A and B represent replicate amplification products evaluated with the $1^{st}$- and $2^{nd}$-strand amplification primers, curves C and D likely represent background product from $1^{st}$-strand synthesis (due to RT strand-displacement), while E and F represent $2^{nd}$-strand synthesis background products. FIG. 4B shows an amplification plot in which curves A and B represent replicate amplification products evaluated with the $1^{st}$- and $2^{nd}$-strand amplification primers, and curves C and D represent reactions performed in the absence of added cDNA library (e.g., "no RNA"). FIG. 4C presents bioanalyzer traces for samples A and B. The arrows point to putative primer dimers.

DETAILED DESCRIPTION

Figure 1A:
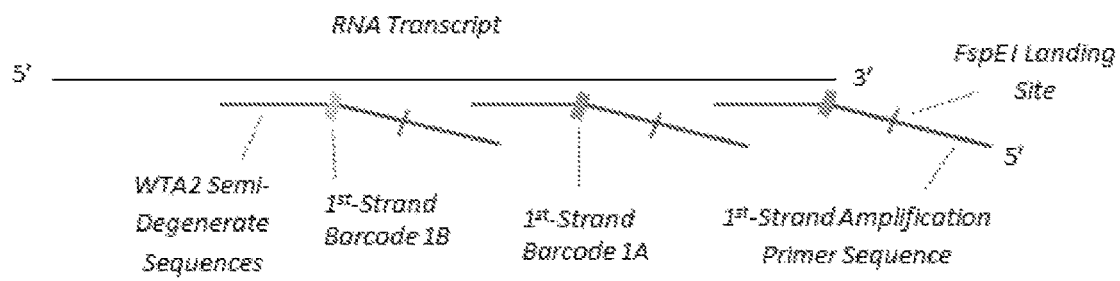
FIGS. 1A-1C present an overview of first strand cDNA synthesis step of the process disclosed herein.

The present disclosure provides processes, oligonucleotides, and kits for generating and amplifying a cDNA library, wherein the orientation or strandedness of the RNA molecule is preserved in the cDNA library products. The orientation of the RNA molecule is indicated by affixing a unique barcode sequence to one or both ends of the cDNA products. The process is sensitive, efficient, and simple. For example, the process is devoid of purification steps, thereby avoiding material loss and allowing for a single-tube format, which is amenable to high throughput. Purification steps are avoided by the step-wise removal of excess primers via 3'-5' exonuclease cleavage and heat denaturation of enzymes. Moreover, the process can be used to amplify small quantities of RNA, as well as low quality RNA. The process also can utilize methylated amplification primers such that terminal amplification primer sequences can be removed by digestion with a methylation dependent restriction enzyme, with no internal cleavage of the amplified products. The unique barcode sequences that indicate orientation of the amplified cDNA library products are not affected by enzyme cleavage.

I. Oligonucleotides

One aspect of the disclosure encompasses an artificial oligonucleotide comprising a fixed 5' sequence, an internal tag sequence, and a random or semi-random 3' sequence. A further aspect provides a plurality of artificial oligonucleotides comprising a plurality of first oligonucleotides and a plurality of second oligonucleotides that may be used for directional amplification of RNA. Each oligonucleotide of the plurality of first oligonucleotides comprises a 5' sequence corresponding to one or more amplification primers; optionally an internal tag sequence comprising a first tag sequence, and a 3' sequence comprising a random or semi-random sequence. Each oligonucleotide of the plurality of second oligonucleotides comprises a 5' sequence corresponding to the one or more amplification primers; optionally an internal tag sequence comprising a second tag sequence, and a 3' sequence comprising a random or semi-random sequence, provided that either one or both of the pluralities of first and second oligonucleotides comprises the internal tag sequence.

In general, the oligonucleotides are single-stranded. The nucleotides can be deoxyribonucleotides or ribonucleotides. The oligonucleotides can comprise the standard four nucleotides (i.e., A, C, G, and T/U), as well as nucleotide analogs. A nucleotide analog refers to a nucleotide having a modified purine or pyrimidine base and/or a modified ribose moiety and/or phosphodiester moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos. The backbone of the oligonucleotides can comprise phosphodiester linkages, as well as phosphothioate, phosphoramidite, or phosphorodiamidate linkages.

(a) 3' Sequence

Each oligonucleotide comprises a random or semi-random 3' sequence. The random or semi-random sequence generally has sufficient complementarity to target nucleic acids such that the 3' sequence of the oligonucleotide hybridizes with the target RNA (or cDNA product). In some embodiments, the 3' sequence can be random and consist of 4-fold degenerate nucleotides (i.e., N). For example, the 3' sequence can be poly-N. In other embodiments, the 3' sequence can be semi-random and comprise at least one 2-fold, 3-fold, or 4-fold degenerate nucleotide. In certain embodiments, the 3' sequence can comprise 2-fold degenerate nucleotides (i.e., K, M, R, Y, and/or S), 3-fold degenerate nucleotides (i.e., B, D, H, and/or V), 4-fold degenerate nucleotides, or combinations thereof. In specific embodiments, the 3' sequence can comprise a combination of N and K (i.e., G and T) degenerate nucleotides. For example, the 3' sequence can comprise about equal numbers of N and K nucleotides that are arranged in any order. Examples of suitable "NK" sequences include 5'-KNNNKNKNK-3', 5'-NNNKNKKNK-3', and 5'-NKNNKNNKK-3'. In additional embodiments, the 3' sequence can comprise a combination of non-degenerate and degenerate nucleotides. For example, the 3' sequence can comprise a poly-dT sequence and degenerate nucleotides at the 3' end. Examples of such sequences include poly-dT-NN, poly-dT-VN, and the like. In still further embodiments, the 3' sequence can comprise a combination of any of the foregoing sequences. As an example, the combination of 5'-KNNNKNKNK-3', 5'-NNN-KNKKNK-3', 5'-NKNNKNNKK-3', and poly-dT$_{14}$-VN are available in the Complete Whole Transcriptome Amplification Kit (WTA2); Sigma-Aldrich.

The length of the 3' sequence can and will vary. In general, the 3' sequence can range from about 5 nucleotides to about 30 nucleotides in length. In certain embodiments, the 3' sequence can be about 5, 6, 7, 8, 9, 10, 11, 12, 13, 14, 15, 16, 17, 18, 19, 20, 21, 22, 23, 24, 25, 26, 27, 28, 29, or 30 nucleotides in length. In specific embodiments, the 3' sequence can range from about 6 to about 20 nucleotides in length.

(b) 5' Sequence

Each oligonucleotide comprises a fixed 5' sequence. The 5' sequence corresponds to one or more amplification primers. Amplification primers are used to amplify DNA during thermocycling reactions. Those skilled in the art are familiar with amplification primer specifications (e.g., GC ratio, Tm, and the like). Amplification primers are commercially available or can be designed for specific applications.

In some embodiments, the 5' sequence comprises a majority (i.e., greater than 50%) of non-complementary nucleotides, thereby reducing intramolecular interactions within each oligonucleotide and/or intermolecular interactions between the 5' sequences in a plurality of oligonucleotides. Examples of non-complementary nucleotides include K (i.e., G and T), M (i.e., A and C), R (i.e., A and G), or Y (i.e., C and T). Thus, in some embodiments, the 5' sequence can comprise at least about 55%, at least about 60%, or at least about 65% of G and T, A and C, A and G, or C and T. In one embodiment, the 5' sequence can comprise at least about 65% of G and T.

In additional embodiments, the 5' sequence can further comprise at least one binding element for a DNA digesting enzyme. The DNA digesting enzyme can be a restriction enzyme (or endonuclease). The restriction enzyme can be naturally occurring, genetically, engineered, or artificial. The restriction enzyme can be a Type I, Type II, Type III, Type IV, or Type V enzyme. The Type II enzyme can be a Type IIB, Type IIE, Type IIF, Type IIG, Type IIM, Type IIS, or Type IIT enzyme. In some embodiments, the restriction enzyme can be a Type IIS enzyme, which cleaves DNA at a defined distance from its non-palindromic asymmetric recognition site. Examples of Type IIS enzymes include FspE1, Fokl, Alwl, and Bfil. In other embodiments, the restriction enzyme can be a methylation-dependent restriction enzyme. Examples of suitable methylation-dependent enzymes include FspEl, LpnPl, McrBC, and MspJl. In still other embodiments, the 5' sequence can contain a hem i-methylated binding site for the methylation-dependent restriction enzyme. For example, the 5' sequence can comprise the hem i-methylated binding site for FspEl, which is shown below:

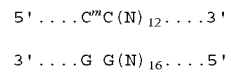

The length of the 5' sequence can and will vary. In general, the 5' sequence can range from about 12 nucleotides to about 36 nucleotides in length. In certain embodiments, the 5' sequence can be about 12, 13, 14, 15, 16, 17, 18, 19, 20, 21, 22, 23, 24, 25, 26, 27, 28, 29, 30, 31, 32, 33, 34, or 35 nucleotides in length. In specific embodiments, the 5' sequence can range from about 15 to about 25 nucleotides in length.

(c) Internal Tag Sequence

Each oligonucleotide also can comprise an optional internal tag (or barcode) sequence. Tag sequences serve to tag cDNA products with respect to the orientation of the starting RNA molecule. If the oligonucleotide contains the optional tag sequence, the tag sequence can be a first tag sequence, which functions to mark the orientation of the 3' end of the RNA, or a second tag sequence, which functions to mark the orientation of the 5' end of the RNA.

The nucleotide sequences of the tag sequences can and will vary. In general, the tag sequences are artificial sequences that are not present in the target RNA molecule (s). The content of nucleotides in the artificial tag sequence can be balanced to provide a diversity of G/T and C/A. Additionally, the first and second oligonucleotides can be balanced per Watson-Crick base pairing to address bias occurring during primer annealing to the target nucleic acid.

In general, the tag sequences can range in length from about 4 nucleotides to about 20 nucleotides. In various embodiments, the tag sequence can range from about 5 nucleotides to about 15 nucleotides in length, from about are 6 nucleotides to about 12 nucleotides in length, or from about 7 nucleotides to about 10 nucleotides in length. In some embodiments, the tag sequence is at least 6 nucleotides in length. In other embodiments, the tag sequence is 7 nucleotides in length, 8 nucleotides in length, or 9 nucleotides in length.

II. Process for Directional Amplification of RNA

Figure 1B:
Figure 1B:
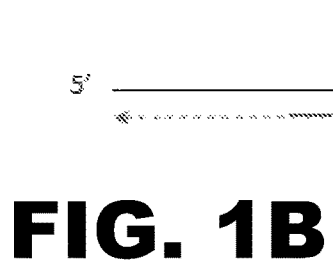
Figure 1C:
Figure 1C:
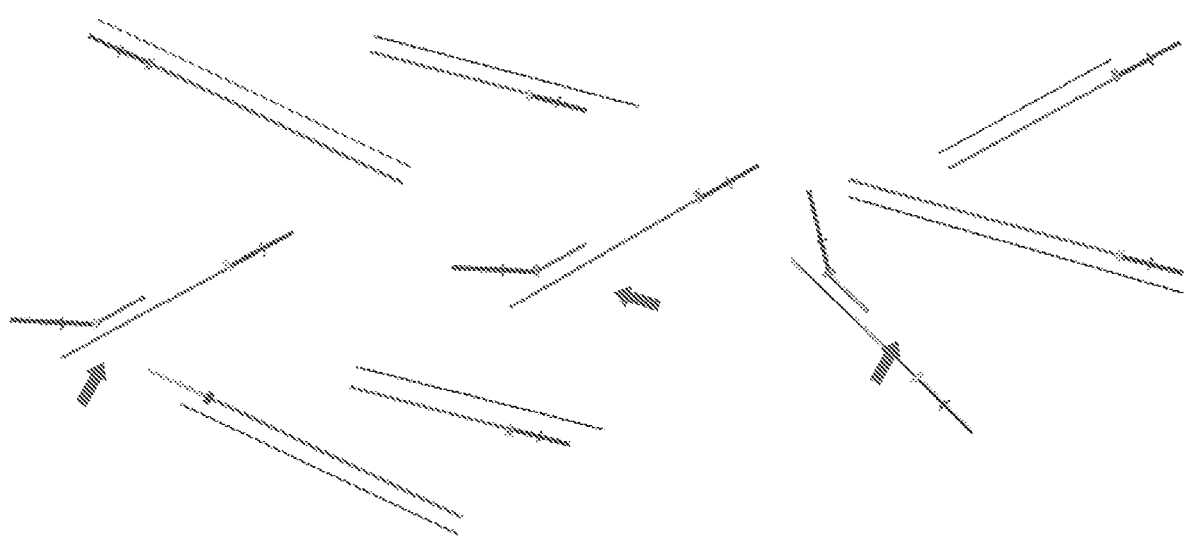
Figure 2A:
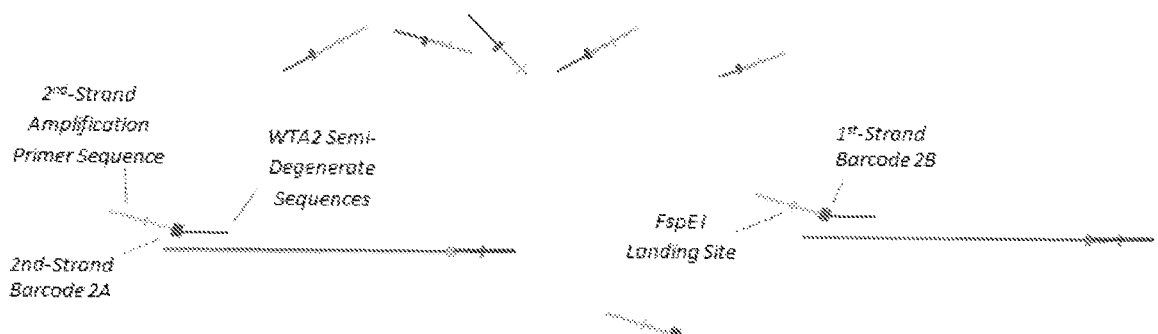
FIGS. 2A-2C illustrate the second strand cDNA synthesis step.
Figure 2B:
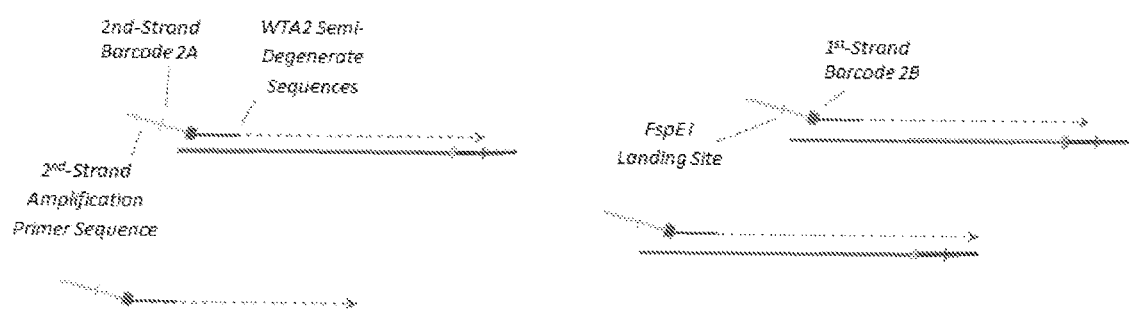
Figure 2C:
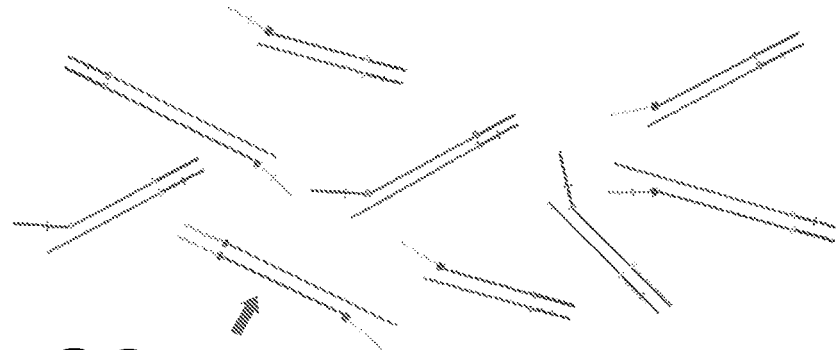
Figure 3A:
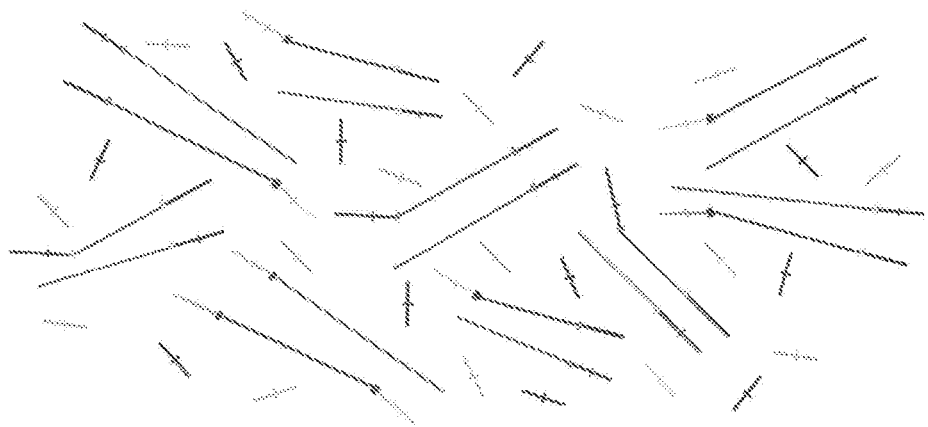
FIGS. 3A-C diagram the amplification step.
Figure 3B:
Figure 3B:
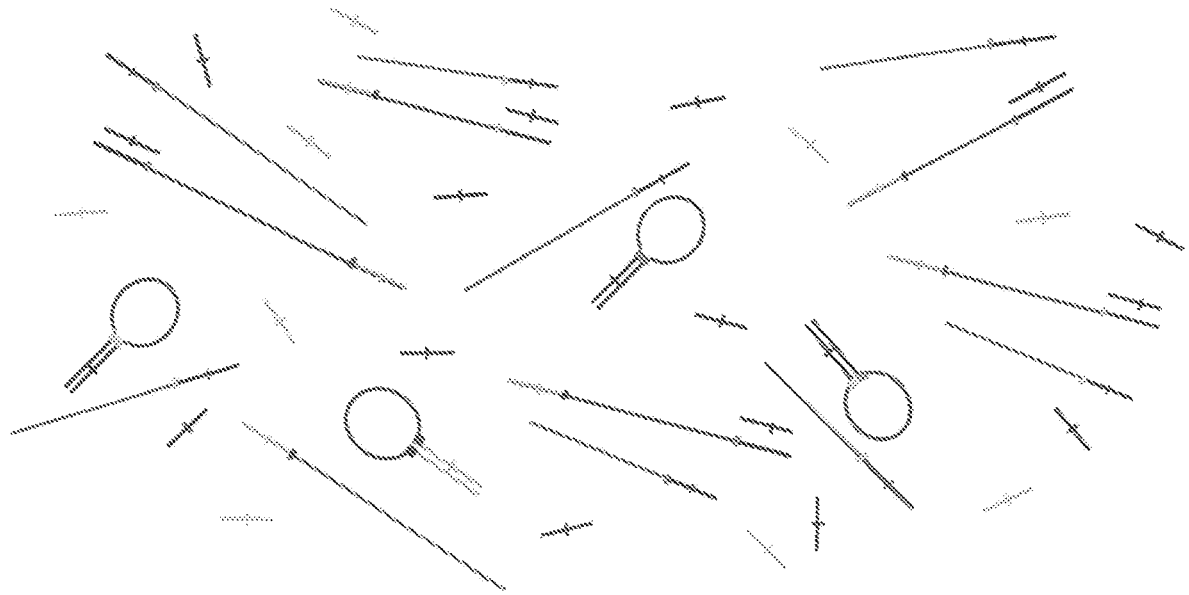
Figure 3C:
Figure 3C:

Another aspect of the disclosure provides a process for directionally amplifying RNA. The process comprises reverse transcribing at least one RNA molecule in the presence of a plurality of first synthesis primers to generate a plurality of first strands of complementary DNA (cDNA), wherein each of the plurality of first synthesis primers comprises a 3' sequence having complementarity to a portion of the RNA molecule, a 5' sequence corresponding to one or more amplification primers, and optionally an internal tag sequence comprising a first tag sequence (FIG. 1A-C). The process further comprises replicating the plurality of first strands of cDNA in the presence of a plurality of second synthesis primers to generate a plurality of double-stranded cDNA products, wherein each of the second synthesis primers comprising a 3' sequence having complementarity to a portion of the first strands of cDNA, a 5' sequence corresponding to the one or more amplification primers, and optionally an internal tag sequence comprising a second tag sequence, provided that either one or both of the pluralities of first and second synthesis primers comprises the internal tag sequence such that each double-stranded cDNA product is flanked by either the first or second tag sequence or both the first and second tag sequences (FIG. 2A-C). Lastly, the process comprises amplifying the plurality of double-stranded cDNA products with one or more amplification primers to generate an amplified library of cDNA products (FIG. 3A-C).

(a) Step a—First Strand cDNA Synthesis

The first step of the process comprises reverse transcribing at least one RNA molecule in the presence of a plurality of first synthesis primers to generate a plurality of first strands of cDNA.

(i) RNA

A variety of different types of RNA molecules can be amplified using the processes disclosed herein. In some embodiments, the RNA can be a messenger RNA (mRNA) or a fragment thereof. The mRNA can be polyadenylated or the mRNA can be non-polyadenylated. In certain embodiments, the RNA can be a population of different mRNAs. In other embodiments, the RNA can be a non-coding RNA (ncRNA). For example, the ncRNA can be long noncoding RNA (lncRNA), long intergenic non-coding RNA (lincRNA), micro RNA (miRNA), small interfering RNA (siRNA), Piwi-interacting RNA (piRNA), trans-acting RNA (rasiRNA), ribosomal RNA (rRNA), transfer RNA (tRNA), mitochondrial tRNA (MT-tRNA), small nuclear RNA (snRNA), small nucleolar RNA (snoRNA), SmY RNA, Y RNA, spliced leader RNA (SL RNA), telomerase RNA component (TERC), fragments thereof, or combinations thereof. In still further embodiments, the RNA can be the transcriptome of a cell or population of cells. The RNA can be derived from eukaryotic, archaeal, or bacterial cells.

The amount of input RNA can and will vary. In general, the processes disclosed herein can amplify low or single cell input quantities of RNA. In some embodiments, the amount of input RNA can be at least about 5 picograms (pg), at least about 10 pg, at least about 20 pg, at least about 50 pg, at least about 100 pg, at least about 200 pg, at least about 500 pg, or more than about 500 pg of RNA. In specific embodiments, the amount of input RNA can range from about 10 pg to about 100 pg.

The quality or integrity of RNA can also vary. For example, the quality of input RNA can range from low quality (i.e., degraded or fragmented) to high quality (i.e., intact). Persons skilled in the art are familiar with means to estimate the quality of the RNA of interest. For example, the quality of total RNA can be estimated on the basis of the ratio of 28S rRNA to 18S rRNA. In some embodiments, the RNA can have a 28S:18S ratio of at least about 2:1, a 28S:18S ratio of at least about 1:1, a 28S:18S ratio of less than about 1:1, or an undetectable 28S:18S ratio.

(ii) First Strand Synthesis

The RNA molecule or molecules are contacted with a plurality of first synthesis primers. The first synthesis primers are detailed above in section (I). Each first synthesis primer comprises a random or semi-random 3' sequence having complementarity to the RNA molecule, a 5' sequence corresponding to one or more amplification primers, and optionally an internal tag sequence comprising a first tag sequence. Upon contact with the target RNA, the 3' sequences of the first synthesis primers hybridize with complementary regions of the RNA (see FIG. 1A). Synthesis of the first strands of cDNA is catalyzed by a reverse transcriptase (RT) in the presence of deoxyribonucleotides (i.e., dCTP, dGTP, dATP, and dTTP) and a suitable RT buffer (see FIG. 1B).

The reverse transcriptase can be mesophilic or thermophilic, and the reverse transcriptase can be RNAaseH$^+$ or RNAaseH$^-$. Examples of suitable reverse transcriptases include M-MLV RT (from Moloney murine leukemia virus), HIV-1 RT (from human immunodeficiency virus type 1), AMV RT (from avian myeloblastosis virus), variants thereof, and engineered versions thereof.

In some embodiments, first strand cDNA synthesis can be conducted in the presence of Actinomycin D to reduce undesired priming from strand-displaced, first strands of cDNA. The use of Actinomycin D can reduce the level of background products flanked with the same sequences (i.e., the product comprises the 5' sequences of the first synthesis primers at both ends; see the arrows in FIG. 1C). Those skilled in the art are familiar with appropriate concentrations of the reactants and suitable reaction conditions for first strand cDNA synthesis.

Upon completion of the first strand synthesis, reaction, the reverse transcriptase can be inactivated by heat treatment. The heat inactivation can be at a temperature of about 70° C., about 80° C., about 90° C., or about 100° C. for about 3 minutes, about 5 minutes, about 10 minutes, or about 15 minutes. In general, the lower the inactivation temperature the longer the duration of the heating step.

(iii) Removal of Single-Stranded First Oligonucleotides

The process further comprises contacting the plurality of first strands of cDNA with a 3'-5' deoxyribonuclease (i.e., exonuclease) to degrade single-stranded (i.e., unhybridized) first synthesis primers (see FIG. 1C). Double-stranded cDNA-RNA hybrids are not degraded by contact with a 3'-5' deoxyribonuclease. In some embodiments, the 3'-5' deoxyribonuclease can be *E. coli* exonuclease I, *E. coli* exonuclease X, or mammalian Trex1 (DNase III). In specific embodiments, the 3'-5' deoxyribonuclease can be *E. coli* exonuclease I. The amount of exonuclease used to degrade the excess first oligonucleotides can and will vary depending upon a variety of factor including the starting quantity of first oligo nucleotides used in step A. In general, contact with the exonuclease is performed at a temperature ranging from about 35° C. to about 40° C. for a period of time from about 5 minutes to about 60 minutes.

(b) Step B—Second Strand cDNA Synthesis

The second step of the process comprises replicating the plurality of first strands of cDNA in the presence of a plurality of second synthesis primers to generate a plurality of double-stranded cDNA products.

(i) Second Strand Synthesis

The plurality of second synthesis primers are described above in section (I). Each second synthesis primer comprises a random or semi-random 3' sequence having complementarity to the first strands of cDNA, a 5' sequence corresponding to the one or more amplification primers, and optionally an internal tag sequence comprising a second tag sequence.

This step of the process commences with heat denaturing the cDNA/RNA duplexes generated during step A in the presence of the plurality of second synthesis primers. The heat treatment generates single-stranded cDNA templates and also inactivates the 3'-5'-exonuclease used to degrade the single-stranded first synthesis primers. The heat treatment can be at a temperature of about 90° C., about 92° C., about 94° C., about 96° C., or about 100° C. for about 1 minute, about 2 minutes, about 5 minutes, or about 10 minutes. After the heat treatment, the temperature is lowered to the reaction temperature and, as the temperature falls, the 3' sequences of the second synthesis primers hybridize with complementary regions of the first strands of cDNA (see FIG. 2A).

Synthesis of the second strand of cDNA is catalyzed by a non-strand-displacing DNA polymerase in the presence of deoxyribonucleotides and a suitable buffer (see FIG. 2B). The non-strand-displacing DNA polymerase can be mesophilic or thermophilic. Examples of suitable non-strand-displacing DNA polymerases include E. coli DNA polymerase I, T4 DNA polymerase, T7 DNA polymerase, variants thereof, and engineered versions thereof. Those skilled in the art are familiar with appropriate concentrations of reactants and suitable reaction conditions for second strand cDNA synthesis. Each double-stranded cDNA product is flanked by the first and second tag sequences, which indicate the orientation of the cDNA product with respect to the input RNA molecule (see FIG. 2C). Second strand synthesis can generate a low level of background products that are flanked with the same sequences (i.e., the product comprises the 5' sequences of the second synthesis primers at both ends; see the arrow in FIG. 2C).

(ii) Optional Removal of Single-Stranded Second Oligonucleotides

The process optionally can further comprise contact with a 3'-5' deoxyribonuclease (i.e., exonuclease) to degrade single-stranded (i.e., unhybridized) second oligonucleotides, essentially as described above in section (II)(a)(iii).

(iii) "Single-Tube" Process

Steps A and B of the process disclosed herein proceed sequentially without intervening purification steps. No purification steps allows for a single tube format, avoiding material loss. A single-tube format is also amenable to high throughput. The lack of purification steps is accomplished by step-wise exonuclease removal of the first and second oligonucleotides, and heat-inactivation of enzymes.

(c) Step C—Amplification

The final step of the process comprises amplifying the plurality of double-stranded cDNA products in the presence of the one or more amplification primers to generate an amplified library of cDNA products.

(i) Reaction

This step commences with heat denaturing the plurality of double-stranded cDNA products generated during step B in the presence of the one or more amplification primers (see FIG. 3A). The heat treatment generates single-stranded templates and also inactivates the 3'-5'-exonuclease used to degrade the single-stranded second oligonucleotides. The heat treatment can be at a temperature of about 90° C., about 92° C., about 94° C., about 96° C., or about 100° C. for about 1 minute, about 2 minutes, about 5 minutes, or about 10 minutes. After the heat treatment, the temperature is lowered to the annealing temperature to permit annealing of the one or more amplification primers to the cDNA template strands. Furthermore, as the temperature falls, intra-molecular hybridization of complementary 3' or 5' sequences at the ends of background products prevents annealing of the amplification primers to the background products (e.g., the stem-loop structures in FIG. 3B). As a consequence, original template and background products are not amplified.

Amplification of the cDNA products is performed in the presence of a thermostable DNA polymerase, deoxyribonucleotides, and a suitable buffer. The thermostable DNA polymerase can be Taq DNA polymerase, Pfu DNA polymerase, Tli (also known as Vent) DNA polymerase, Tfl DNA polymerase, Tth DNA polymerase, variants thereof, and combinations thereof. Buffers (with or without magnesium) suitable for a thermocycling reaction are well known in the art.

In embodiments in which a single amplification primer is used, the process can comprise 3 steps (i.e., denaturation, annealing, and extension) or 2 steps (i.e., denaturation and annealing/extension). For example, in embodiments in which the melting temperature of the amplification primer is lower than 70° C., the amplification process can comprise 3 steps. Alternatively, in embodiments in which the melting temperature of the amplification primer is equal to or higher than 70° C., the amplification process can comprise 2 steps. In embodiments in which more than one amplification primer is used, the process generally comprises 3 steps (i.e., denaturation, annealing, and extension). The temperature of the annealing or annealing/extension step can and will vary, e.g., from about 50° C. to about 75° C. The temperature of the extension or annealing/extension can range from about 70° C. to about 75° C., or about 72° C. The duration of the steps of the amplification can vary from seconds to minutes. In general, the duration of the extension or annealing/extension step can range from 1 to 5 minutes.

(ii) Amplification Primers

In general, the amplification is performed in the presence of one or more amplification primers. As detailed above, the 5' sequence of the first and second synthesis primers corresponds to the one or more amplification primers. For example, a single amplification primer can correspond to the fixed 5' sequence of the first and second synthesis primers. In other embodiments, the additional amplification primers can correspond to truncated versions of the fixed 5' sequence of the first and second synthesis primers.

In general, the amplification primers are single-stranded and comprise deoxyribonucleotides. The deoxyribonucleotides can comprise the standard four nucleotides (i.e., A, C, G, and T), as well as nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids, peptide nucleic acids, and morpholinos. The backbone of the amplification primers can comprise phosphodiester linkages, as well as phosphothioate, phosphoramidite, or phosphorodiamidate linkages.

In embodiments in which the fixed 5' sequences of the first and second synthesis primers contain at least one binding element for a methylation-dependent DNA digesting enzyme, the one or more amplification primers can contain methylated nucleotides in the binding element. For example, the one or more amplification primers can contain at least one methylated cytosine, e.g., 5-methylcytosine or 3-methylcytosine. In some embodiments, the methylated C can follow C (i.e., C$^m$C), the methylated C can be followed by G (i.e., $^m$CG), or the methylated C can be followed by HG or HH, wherein in H is A, C, or T (i.e., $^m$CHG, $^m$CHH). In specific embodiments, the one or more amplification primers can contain a methylated C in the binding element, wherein the methylated sequence can be C$^m$CG, C$^m$CHG, or C$^m$CHH.

(iii) Post Reaction

Upon completion of the amplification reaction, the amplified cDNA library can be purified from the reaction reactants and excess amplification primers using means well known in the art. For example, using chromatography-based and/or magnetic bead-based methods.

The yield of the amplified cDNA library can and will vary depending, for example, on the amount of input RNA and the efficiency of the various reactions. In general, the yield of the amplified cDNA library can be at least about 1 µg, at least about 2 µg, at least about 3 µg, at least about 4 µg, or at least about 5 µg.

(ii) Downstream Applications

In embodiments in which the constant 5' sequences of the first and second synthesis primers and the one or more amplification primers comprise at least one binding element for a the DNA digesting enzyme (or restriction endonuclease), the products of the amplified cDNA library are flanked by binding and recognition sites for the restriction endonuclease. Digestion of the amplified cDNA library with the restriction endonuclease will remove the majority of the constant sequences at the ends of the cDNA library products while maintaining the unique tag or barcode sequences at one or both ends of the cDNA library products. Thus, the "strandedness" of the cDNA products is preserved. The use of a methylation-dependent restriction endonuclease and methylated amplification primers ensures that the only sequences cleaved by the restriction endonuclease are the methylated (or hemi-methylated) sequences within the constant sequences at the ends of the cDNA library products. There is no internal cleavage. The digested cDNA library products can be purified from the released fragments using standard procedures. Furthermore, the digested cDNA library products can be processed for a sequencing reaction by subjecting them to a fill-in reaction and a dA-tailing reaction using commonly known procedures. In other embodiments, custom sequencing adaptors (e.g., Illumina adaptor sequences) can be incorporated by PCR to the amplified (undigested) amplified cDNA library products. Following cluster formation, the directional amplification primers serve as Read 1 and Read 2 primers.

The amplified cDNA library can be sequenced by a variety of sequencing procedures including directional deep sequencing, next generation sequencing, Illumina sequencing, 454 sequencing, ion torrent sequencing, SOLiD sequencing, nanoball sequencing, single molecule read time sequencing, and the like. The amplified cDNA library can also be used in other well-known PCR-based applications.

III. Kits

Still another aspect of the present disclosure provides kits comprising the oligonucleotides described above in section (I), or kits for amplifying RNA using the processes detailed above in section (II).

In some embodiments, the kits can comprise (a) a plurality of first synthesis primers in which each first synthesis primer comprises a 5' sequence correspond to one or more amplification primers, optionally an internal tag sequence comprising a first tag sequence, and a random or semi-random 3' sequence, (b) a plurality of second synthesis primers in which each second synthesis primer comprises a 5' sequence corresponding to the one or more amplification primers, optionally an internal tag sequence comprising a second tag sequence, and a random or semi-random 3' sequence, provided that either one or both of the pluralities of first and second synthesis primers comprises the internal tag sequence, and (c) the one or more second amplification primers. The first and second synthesis primers are the oligonucleotides described above in section (I).

The kits can further comprise a reverse transcriptase as described in section II(a), a non-strand-displacing DNA polymerase as described in section II(b), a 3'-5' deoxyribonuclease as described in section I(a), a thermophilic DNA polymerase as described in section II(c)(ii), a DNA digesting enzyme as described in section (I)(a)(ii), and/or Actinomycin D.

Any of the kits can further comprise deoxyribonucleotides and one or more suitable buffers (e.g., a reverse transcriptase buffer, a second strand synthesis buffer, a thermocycling buffer, and the like).

The kits provided herein generally include instructions for carrying out the processes detailed above. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

As various changes could be made in the above-described processes and kits without departing from the scope of the disclosure, it is intended that all matter contained in the above description and in the examples given below, shall be interpreted as illustrative and not in a limiting sense.

Definitions

Unless defined otherwise, all technical and scientific terms used herein have the meaning commonly understood by a person skilled in the art to which this disclosure belongs. The following references provide one of skill with a general definition of many of the terms used herein: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

A degenerate nucleotide can have 2-fold degeneracy (i.e., it can be one of two nucleotides), 3-fold degeneracy (i.e., it can be one of three nucleotides), or 4-fold degeneracy (i.e., it can be one of four nucleotides. A or C or G or T). Nucleotides having 3-fold degeneracy include "B" (can be C or G or T), "D" (can be A or G or T), "H" (can be A or C or T), and "V" (can be A or C or G). Nucleotides having 2-fold degeneracy include "K" (can be G or T), "M" (can be A or C), "R" (can be A or G), "Y" (can be C or T), "S" (can be C or G), and "W" (can be A or T).

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

EXAMPLES

The following example illustrates certain aspects of the disclosure.

Example 1: Amplification of Universal Human Reference (UHR) RNA

Figure 4A:
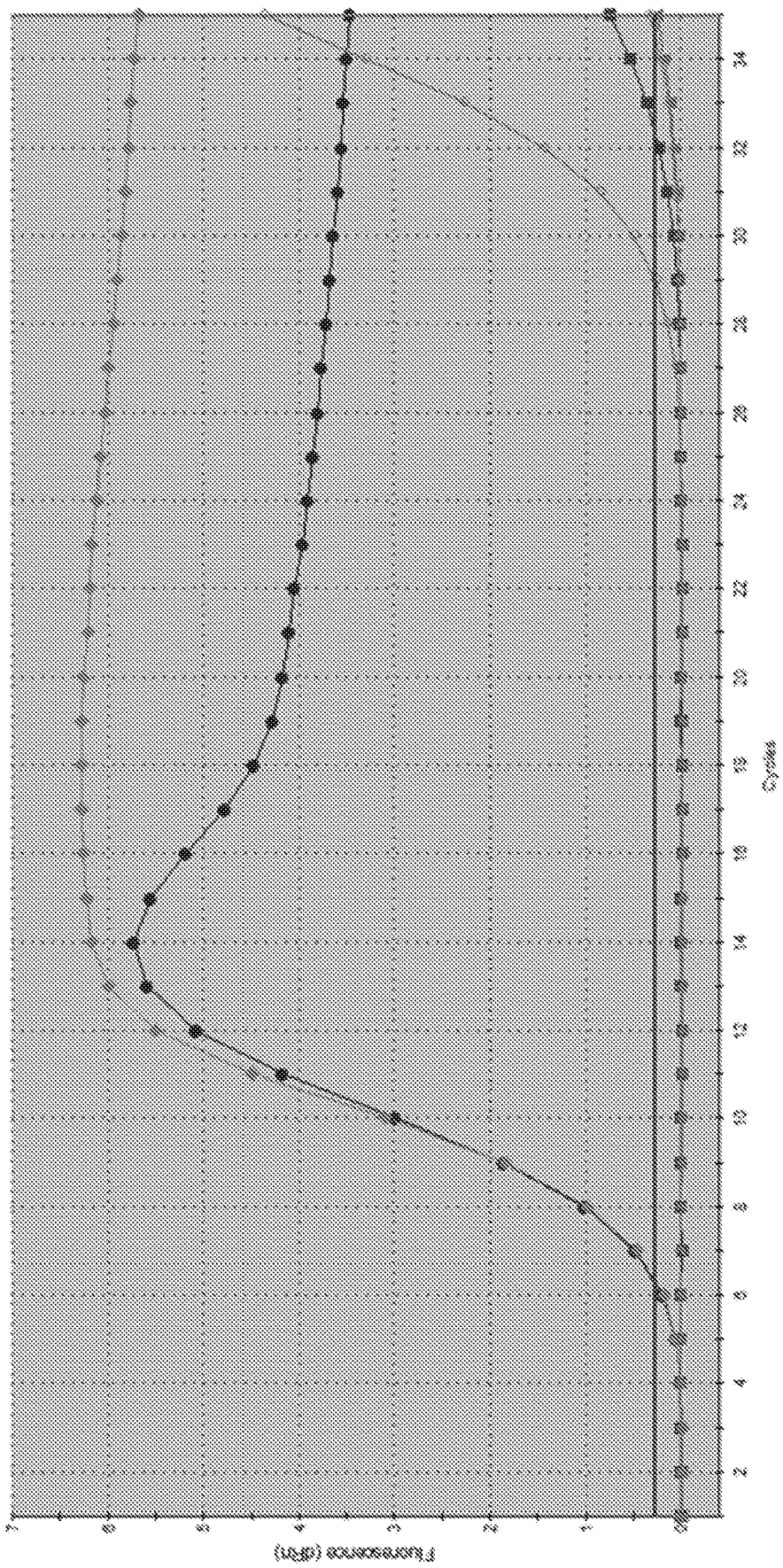
FIGS. 4A-C illustrate endpoint pPCR analysis of amplified cDNA products prepared from UHR RNA.

UHR RNA was amplified "to plateau" using the first process outlined above. Endpoint qPCR analysis of amplification product is shown in FIG. 4A. Curves A and B represent replicate amplification products evaluated with the $1^{st}$- and $2^{nd}$-strand amplification primers. Curves C and D likely represent background product from $1^{st}$-strand synthesis (due to RT strand-displacement), while E and F represent $2^{nd}$-strand synthesis background product.

The delta between the average C(t) for 1st-strand background and amplification product, (C/D)-(A/B), was 27.1, and the delta C(t) for 2nd-strand background and amplification product, (E/F)-(A/B), was 22.62. The large deltas for this end product analysis reflects how comparatively little background product was present at the end of amplification.

Figure 4B:
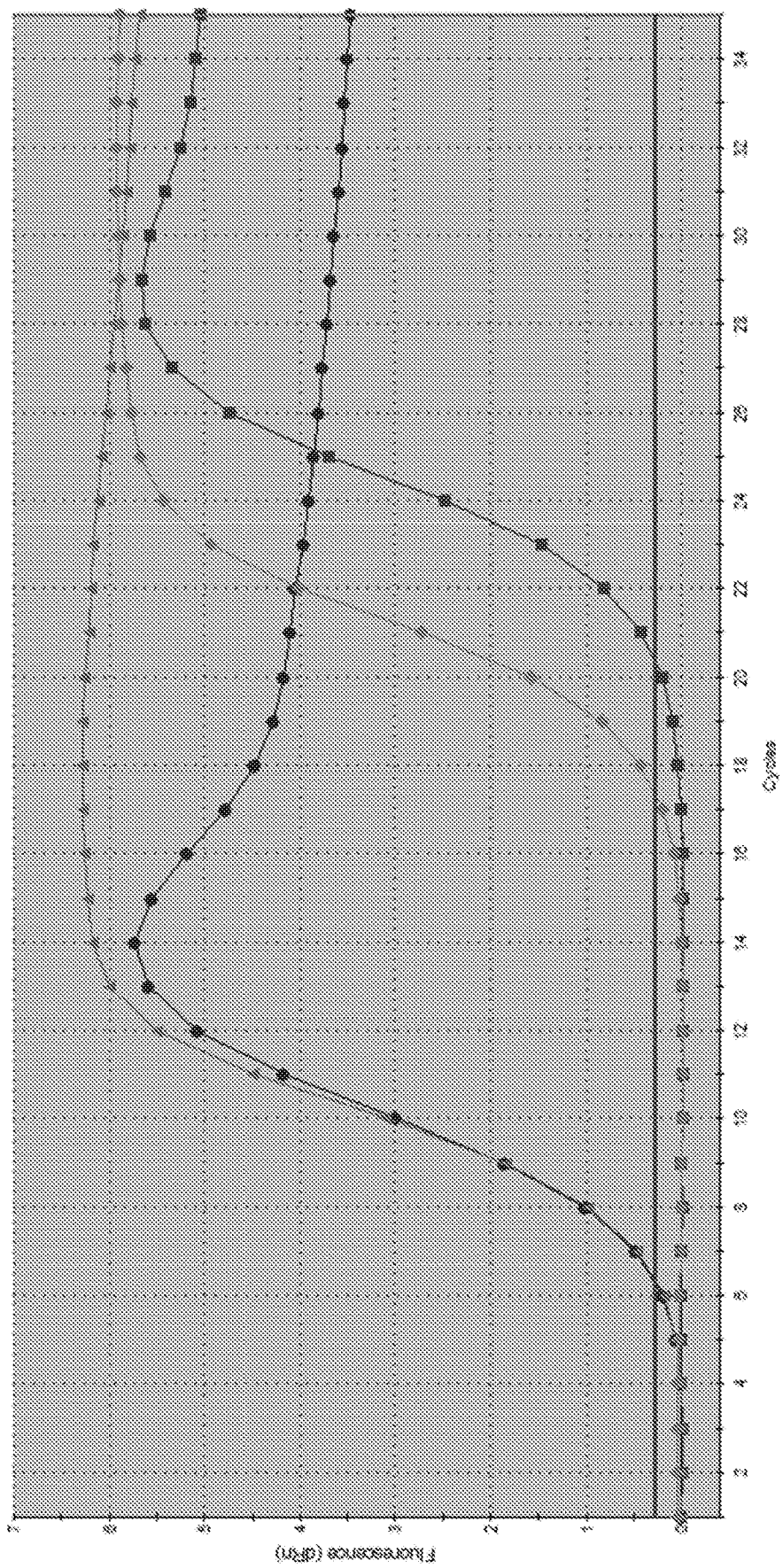

FIG. 4B presents a comparison of the curves for replicate amplification products A and B, relative to "no RNA" control reactions. Curves C and D are replicate qPCR reactions in which no cDNA library was added, only the amplification primers. It is hypothesized that C and D may represent some type of primer dimer interaction.

Figure 4C:
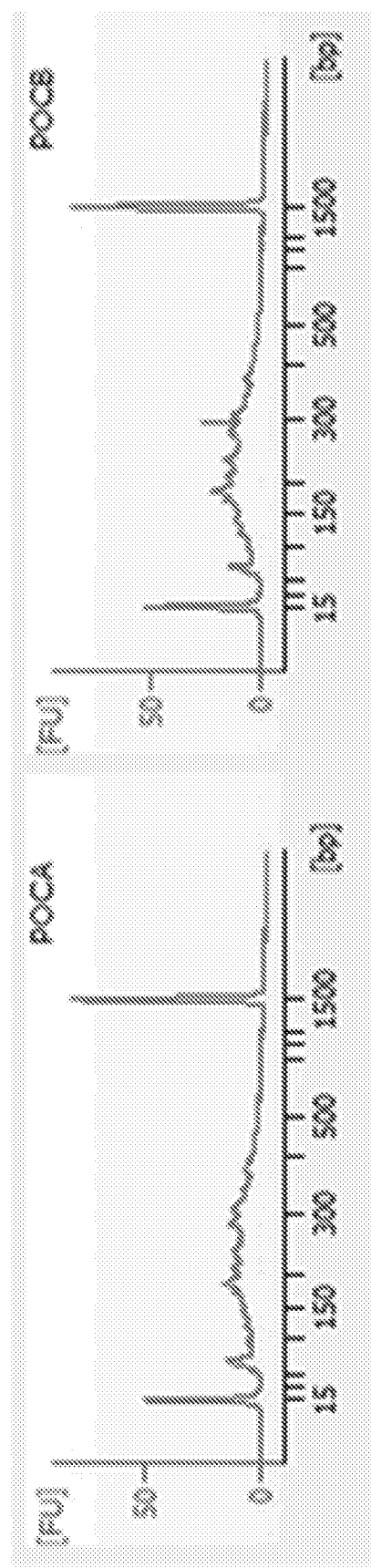

The average endpoint delta in this experiment was 12.525, indicative of a low contribution to the final quantity of amplification product. However, because this was an end-point analysis, primer dimers do accumulate and appear in the Bioanalyzer traces for these samples, as shown in FIG. 4C.

What is claimed is:

1. A process for directionally amplifying RNA, the process comprising:
   (a) reverse transcribing at least one RNA molecule in the presence of a plurality of first synthesis primers to generate a plurality of first strands of complementary DNA (cDNA), each of the first synthesis primers comprising a 3' sequence having complementarity to a portion of the RNA molecule, a 5' sequence corresponding to one or more methylated amplification primers, and optionally an internal tag sequence comprising a first tag sequence;
   (b) replicating the plurality of first strands of cDNA in the presence of a plurality of second synthesis primers to generate a plurality of double-stranded cDNA products, each of the second synthesis primers comprising a 3' sequence having complementarity to a portion of the first strands of cDNA, a 5' sequence corresponding to the one or more methylated amplification primers, and optionally an internal tag sequence comprising a second tag sequence, provided that either one or both of the pluralities of first and second synthesis primers comprises the internal tag sequence such that each double-stranded cDNA product is flanked by either the first or second tag sequence or both the first and second tag sequences; and (c) amplifying the plurality of double-stranded cDNA products in the presence of the one or more methylated amplification primers to generate an amplified library of cDNA products;

wherein the 5' sequence of the first and second synthesis primers further comprises at least one binding element for a methylation-dependent restriction enzyme, and wherein the amplified library of cDNA products is contacted with the methylation-dependent restriction enzyme.

2. The process of claim 1, wherein the 3' sequence of the first and second synthesis primers is random, semi-random, or a combination thereof.

3. The process of claim 1, wherein the binding element is hemi-methylated.

4. The process of claim 1, wherein the 5' sequence of the first and second synthesis primers comprises a majority of non-complementary nucleotides.

5. The process of claim 1, wherein the first and/or second tag sequences are at least 6 nucleotides in length.

6. The process of claim 1, wherein step (a) is conducted in the presence of a reverse transcriptase, deoxyribonucleotides, and optionally Actinomycin D.

7. The process of claim 1, wherein step (a) is followed by contact with a 3'-5' deoxyribonuclease to degrade unhybridized first synthesis primers.

8. The process of claim 1, wherein step (b) commences with heat denaturation of the plurality of first strands of cDNA in the presence of the plurality of second synthesis primers, and step (b) is conducted in the presence of a non-strand-displacing DNA polymerase and deoxyribonucleotides.

9. The process of claim 1, wherein step (b) optionally is followed by contact with a 3'-5' deoxyribonuclease to degrade unhybridized second oligonucleotides.

10. The process of claim 1, wherein step (c) commences with heat denaturation of the plurality of double-stranded cDNA products in the presence of the one or more amplification primers, and step (c) is conducted in the presence of a thermostable DNA polymerase and deoxyribonucleotides.

11. The process of claim 1, further comprising incorporating adaptor sequences to the 5' ends of the amplified library of cDNA products.

12. The process of claim 1, which is devoid of one or more purification steps between steps (a) and (b) and/or between steps (b) and (c).

* * * * *